United States Patent
Lindquist et al.

(10) Patent No.: US 10,543,039 B2
(45) Date of Patent: Jan. 28, 2020

(54) NERVE ABLATION DEVICES AND RELATED METHODS OF USE AND MANUFACTURE

(71) Applicant: BOSTON SCIENTIFIC SCIMED, INC., Maple Grove, MN (US)

(72) Inventors: Jeffrey S. Lindquist, Maple Grove, MN (US); Joseph Zielinski, Plymouth, MN (US); Mark S. Smith, Coon Rapids, MN (US); Kevin Martin, Maple Grove, MN (US); Joel R. Munsinger, Blaine, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 595 days.

(21) Appl. No.: 14/657,622

(22) Filed: Mar. 13, 2015

(65) Prior Publication Data

US 2015/0265339 A1 Sep. 24, 2015

Related U.S. Application Data

(60) Provisional application No. 61/955,097, filed on Mar. 18, 2014, provisional application No. 62/032,778, filed on Aug. 4, 2014.

(51) Int. Cl.
*A61B 18/14* (2006.01)
*A61B 18/00* (2006.01)

(52) U.S. Cl.
CPC .. *A61B 18/1492* (2013.01); *A61B 2018/0022* (2013.01); *A61B 2018/00434* (2013.01)

(58) Field of Classification Search
CPC ...... A61B 18/1492; A61B 2018/00136; A61B 2018/0022; A61B 2018/00404; A61B 2018/00434; A61B 2018/00511
See application file for complete search history.

(56) References Cited

U.S. PATENT DOCUMENTS

| | | | | |
|---|---|---|---|---|
| 6,332,881 | B1* | 12/2001 | Carner | A61B 18/1402 606/41 |
| 2006/0173511 | A1* | 8/2006 | Greenberg | A61N 1/0543 607/54 |
| 2008/0156437 | A1* | 7/2008 | Kawate | H01R 12/61 156/330 |
| 2012/0071870 | A1* | 3/2012 | Salahieh | A61B 5/01 606/33 |

* cited by examiner

*Primary Examiner* — Daniel W Fowler
*Assistant Examiner* — Tigist S Demie (57) ABSTRACT

A medical device for sympathetic nerve ablation includes a catheter shaft and an expandable member disposed on the catheter shaft. The balloon is configured to be able to shift between an unexpanded configuration and an expanded configuration. The medical device includes an elongate electrode assembly constructed as a flexible circuit and a protective bumper member. The elongate electrode assembly may have an outer edge and may be disposed on an outer surface of the balloon. The protective bumper member may cover at least a portion of the outer edge of the elongate electrode assembly.

20 Claims, 10 Drawing Sheets

NERVE ABLATION DEVICES AND RELATED METHODS OF USE AND MANUFACTURE

CROSS-REFERENCE TO RELATED APPLICATIONS

This application claims priority under 35 U.S.C. § 119 to U.S. Provisional Application Ser. No. 61/955,097, filed Mar. 18, 2014, and to U.S. Provisional Application Ser. No. 62/032,778, filed Aug. 4, 2014, the entirety of both of which are incorporated herein by reference.

TECHNICAL FIELD

The present disclosure pertains to medical devices, and methods for using and manufacturing medical devices. More particularly, the present disclosure pertains to medical devices and methods that relate to nerve ablation.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

Medical devices and methods for making and using medical devices are disclosed herein. An example medical device for sympathetic nerve ablation is disclosed. The medical device comprises:
 a catheter shaft;
 an expandable balloon disposed on the catheter shaft, the balloon being capable of shifting between an unexpanded configuration and an expanded configuration;
 an elongate electrode assembly constructed as a flexible circuit, the elongate electrode assembly disposed on an outer surface of the balloon and having an outer edge; and
 a protective bumper member covering at least a portion of the outer edge of the elongate electrode assembly.

Alternatively or additionally to any of the embodiments above, the protective bumper member comprises a polymeric material.

Alternatively or additionally to any of the embodiments above, the protective bumper member comprises a light curable adhesive.

Alternatively or additionally to any of the embodiments above, the protective bumper member is formed of an adhesive having a viscosity greater than about 6000 centiPoise.

Alternatively or additionally to any of the embodiments above, the bumper member is formed of an adhesive having a viscosity greater than about 10,000 centiPoise.

Alternatively or additionally to any of the embodiments above, the protective bumper member covers substantially all of the outer edge of the elongate electrode assembly.

Alternatively or additionally to any of the embodiments above, at least a portion of a bottom side of the elongate electrode assembly is attached to the outer surface of the balloon.

Alternatively or additionally to any of the embodiments above, the balloon is a non-compliant balloon and the elongate electrode assembly folds and unfolds with the balloon.

Alternatively or additionally to any of the embodiments above, the balloon is a compliant balloon and the elongate electrode assembly folds and unfolds with the balloon.

Alternatively or additionally to any of the embodiments above, the balloon comprises polyethyleneterephthalate (PET).

A medical device for sympathetic nerve ablation is disclosed. The medical device comprises:
 a catheter shaft;
 an expandable member coupled to the catheter shaft, the expandable member being capable of shifting between an unexpanded configuration and an expanded configuration; and
 an elongate electrode assembly constructed as a flexible circuit having a plurality of layers and an outer edge, the elongate electrode assembly disposed on an outer surface of the expandable member; and
 a protective bumper member extending about the outer edge of the flexible circuit.

Alternatively or additionally to any of the embodiments above, the protective bumper member covers the outer edge and a portion of an outer periphery of the flexible circuit.

Alternatively or additionally to any of the embodiments above, the protective bumper member comprises a polymeric material.

Alternatively or additionally to any of the embodiments above, the protective bumper member comprises a light curable adhesive.

Alternatively or additionally to any of the embodiments above, the protective bumper member is formed of an adhesive having a viscosity greater than about 6000 centiPoise.

Alternatively or additionally to any of the embodiments above, the protective bumper member is formed of an adhesive having a viscosity greater than about 10,000 centiPoise.

Alternatively or additionally to any of the embodiments above, the balloon is a non-compliant balloon and the elongate electrode assembly folds and unfolds with the balloon.

A medical device for sympathetic nerve ablation within a body passageway is disclosed. The medical device comprises:
 a catheter shaft;
 an elongate balloon coupled to the catheter shaft, the balloon being capable of shifting between an unexpanded configuration and an expanded configuration;
 a plurality of electrode assemblies each constructed as a flexible circuit having a plurality of layers, the plurality of electrode assemblies being bonded to an outer surface of the balloon, each of the plurality of electrode assemblies including an outer edge; and
 a plurality of protective polymeric bumper members, each of the plurality of protective polymeric bumper members surrounding the outer edge of a corresponding one of the plurality of electrode assemblies.

Alternatively or additionally to any of the embodiments above, at least some of the plurality of raised protective bumpers are formed of an adhesive having a viscosity greater than about 6000 centiPoise.

Alternatively or additionally to any of the embodiments above, the balloon is a non-compliant balloon.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

Definitions of certain term are provided below, and these definitions shall be applied, unless a different definition is given in the claims or elsewhere in this specification.

All numeric values used herein are assumed to be modified by the term "about," whether or not explicitly indicated. The term "about" generally refers to a range of numbers that one of skill in the art would consider equivalent to the recited value (i.e., having the same or substantially the same function or result). In many instances, the terms "about" may include numbers that are rounded to the nearest significant figure. The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents, unless the content clearly dictates otherwise. As used in this specification and the appended claims, the term "or" is generally employed in its sense including "and/or", unless the content clearly dictates otherwise.

The following detailed description should be read with reference to the drawings in which similar elements in different drawings are identified with the same reference numbers. The drawings, which are not necessarily to scale, depict illustrative embodiments and are not intended to limit the scope of the invention.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure, or characteristic is described in connection with one embodiment, it should be understood that such feature, structure, or characteristic may also be used in connection with other embodiments, whether or not explicitly described, unless cleared stated to the contrary.

Certain treatments may require the temporary or permanent interruption or modification of select nerve function. One exemplary treatment is renal nerve ablation, which is sometimes used to treat conditions related to hypertension and/or congestive heart failure. The kidneys produce a sympathetic response to congestive heart failure, which, among other effects, increases the undesired retention of water and/or sodium. Ablating some of the nerves running to the kidneys may reduce or eliminate this sympathetic function, which may provide a corresponding reduction in the associated undesired symptoms.

Many nerves (and nervous tissue, such as brain tissue), including renal nerves, run along the walls of, or in close proximity to, blood vessels, and thus can be accessed intravascularly through the walls of the blood vessels. In some instances, it may be desirable to ablate perivascular nerves using a radio frequency (RF) electrode. In other instances, the perivascular nerves may be ablated by other techniques or devices, including application of thermal, ultrasonic, laser, microwave, and other related energy sources to the vessel wall.

Figure 1:
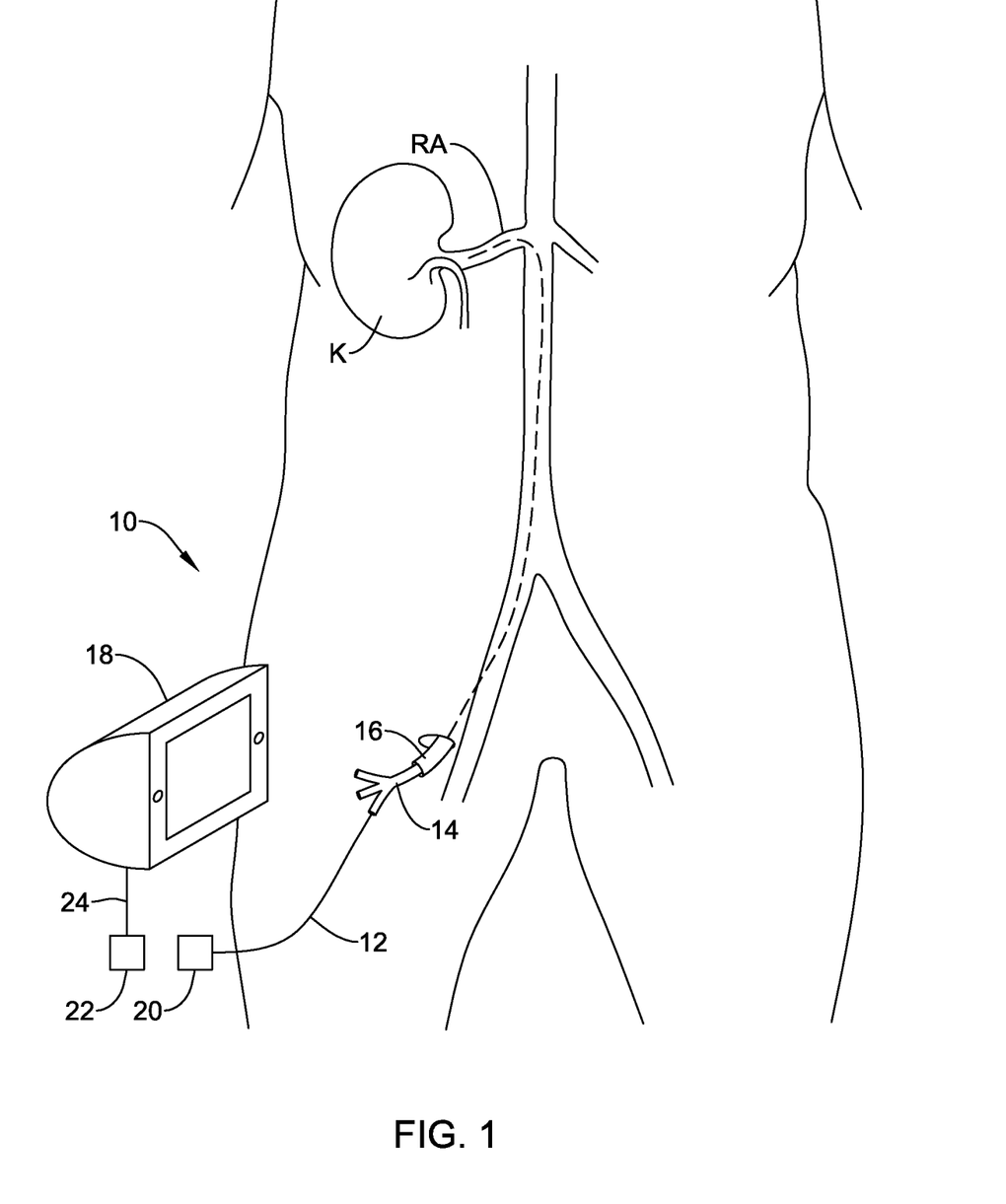
FIG. 1 is a schematic view illustrating an exemplary renal nerve ablation system, according to some embodiments of the present disclosure.

FIG. 1 is a schematic view of an illustrative renal nerve ablation system 10 in situ. In the illustrated embodiment, the system 10 is used to ablate one or more renal nerves of a right kidney K. In the illustrated embodiment, only the right kidney K is shown for purposes of simplicity of explanation, however, the system 10 can be used for both right and left kidneys, and associated renal vasculature, such as the renal artery RA that branches laterally from the abdominal aorta.

In general, system 10 may include one or more conductive element(s) 12 providing power to renal ablation system 14 disposed within a sheath 16. Although not shown, a proximal end of conductive element 12 may be connected to a control and power element 18, which supplies the necessary electrical energy to activate one or more electrodes at or near a distal end of the renal ablation system 10. The system 10 further includes two or more connectors 20 and 22 that may provide connection between the conductive element 12 and the control and power element 18 through a connective link 24, which can be a wire, for example. The control and power element 18 may include monitoring elements to monitor parameters, such as power, temperature, voltage, pulse size and/or shape and other suitable parameters as well as suitable controls for performing the desired procedure. The control and power element 18 may control a radio frequency (RF) electrode, which may be configured to operate at a frequency of approximately 460 kHz. It is contemplated that any desired frequency in the RF range may be used, for example, from 450-500 kHz. However, different types of energy outside of the RF spectrum may be used as desired, for example, but not limited to, ultrasound, microwave, and laser technologies.

Figure 2:
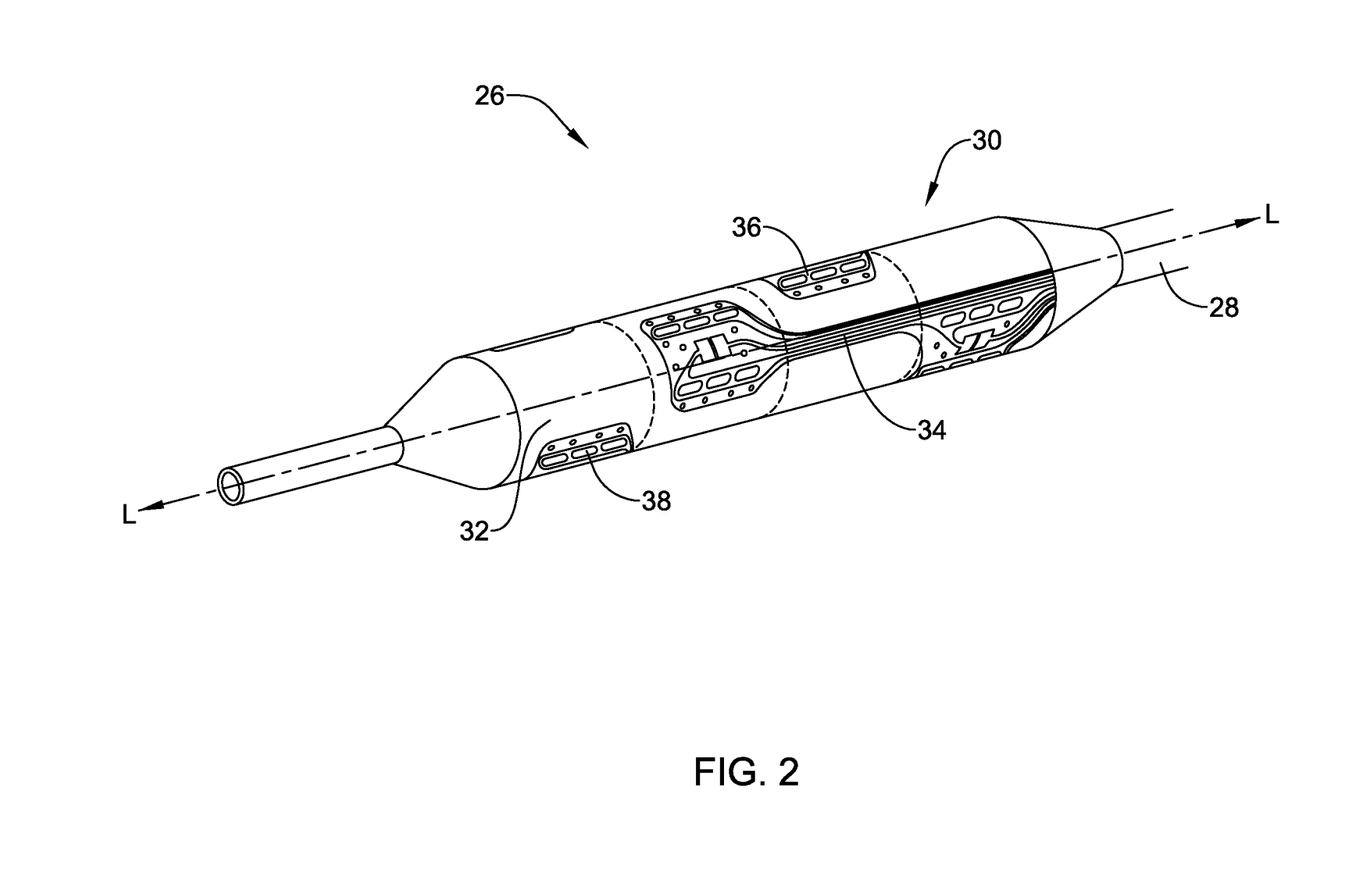
FIG. 2 is a schematic view illustrating an exemplary sympathetic nerve ablation device, in accordance with the present disclosure.

FIG. 2 is a schematic view illustrating a portion of an example renal nerve ablation device 26. In particular, the device 26 includes a catheter shaft 28 having an expandable member 30 coupled to the catheter shaft 28. In the illustrated embodiment, the expandable member 30 is a balloon; however, those skilled in the art will appreciate that other suitable expandable members, such as members formed at least partially of mesh, etc., can also be used.

Although not shown, the catheter shaft 28 may have a proximal region that may extend proximally to remain outside of the patient's body, whereas a distal region having the expandable member 30 is configured to be inserted into the patient's body. The catheter shaft 28 may also include one or more lumens (not shown) extending between the proximal and distal regions, where the catheter shaft 28 may be adapted to enter a patient's body. Specifically, the distal region of the catheter shaft 28 may be advanced within the patient's body to reach a target site. In certain instances, the proximal region of the catheter shaft 28 may include a hub attached thereto for connecting to other diagnostic and/or treatment devices, which provides a port for facilitating other interventions.

The device further includes several elongate electrode assemblies that may be disposed about an outer surface 32 of the expandable member 30. Any number of elongate electrode assemblies may be disposed about outer surface 32. In FIG. 2, one elongate electrode assembly 34 may be seen in its entirety, and portions of an elongate electrode assembly 36 and an elongate electrode assembly 38 can be seen.

Figure 3:
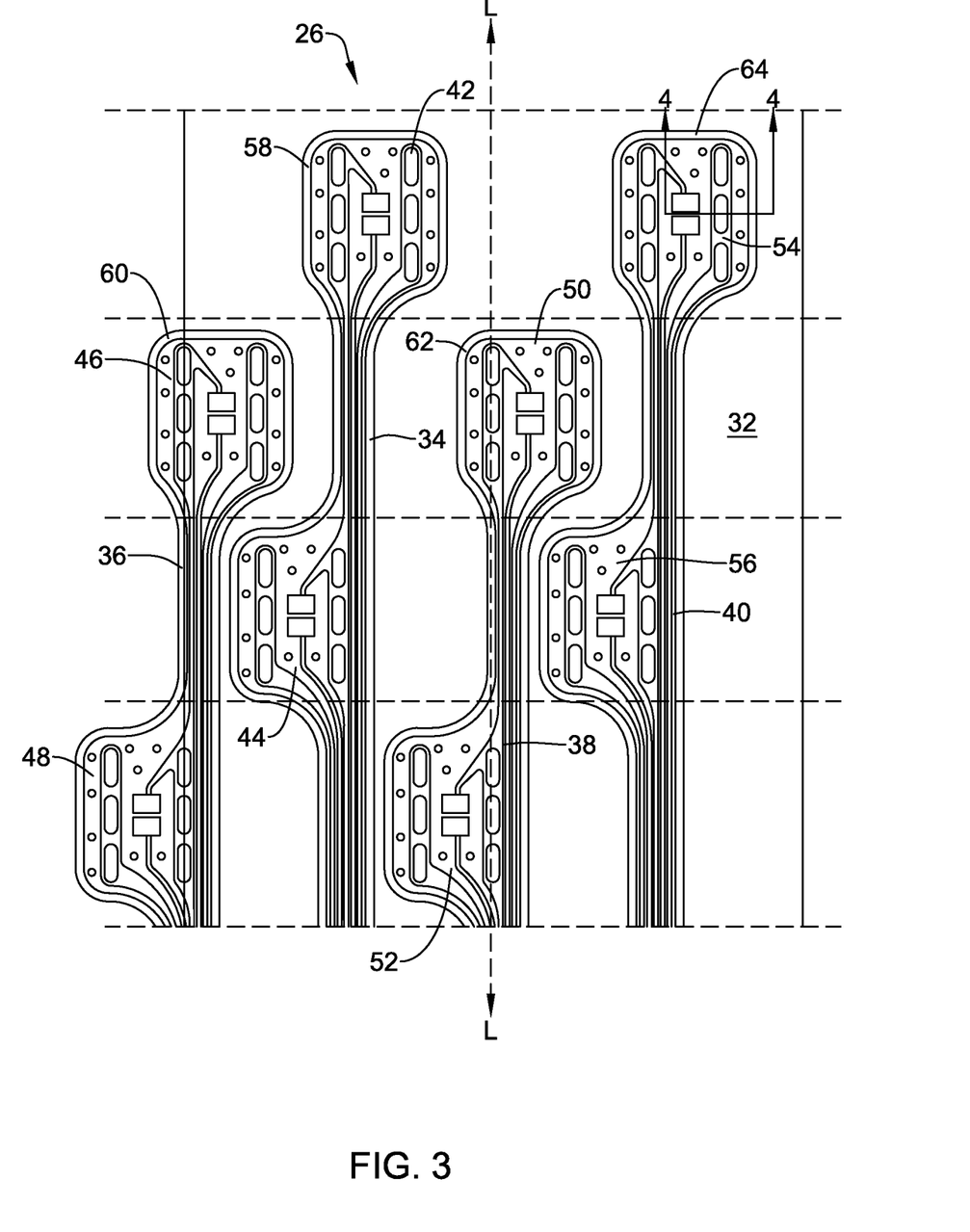
FIG. 3 is a schematic top view illustrating a flattened view of the sympathetic nerve ablation device of FIG. 2.

FIG. 3 provides a flattened view of outer surface 32 and thus illustrates more of outer surface 32. As illustrated, device 26 includes elongate electrode assembly 34, elongate electrode assembly 36, elongate electrode assembly 38 and elongate electrode assembly 40. It will be appreciated that device 26 may include more than four elongate electrode assemblies. In some embodiments, device 26 may include fewer than four elongate electrode assemblies.

In the illustrated embodiment, elongate electrode assembly 34 includes a distal pad 42 and a proximal pad 44. Elongate electrode assembly 36 includes a distal pad 46 and a proximal pad 48. Elongate electrode assembly 38 includes a distal pad 50 and a proximal pad 52. Elongate electrode assembly 40 includes a distal pad 54 and a proximal pad 56. While not expressly called out, it will be appreciated that each of distal pads 42, 46, 50 and 54 and each of proximal pads 44, 48, 52 and 56 include one or more layers in their construction and one or more conductive traces disposed within the one or more layers.

In some embodiments, device 26 includes one or more bumper members that at least partially cover an edge of one or more of the elongate electrode assemblies. As seen in FIG. 3, a protective bumper member 58 surrounds elongate electrode assembly 34, a protective bumper member 60 surrounds electrode assembly 36, a protective bumper member 62 surrounds electrode assembly 38 and a protective bumper member 64 surrounds electrode assembly 40. While each protective bumper member 58, 60, 62 and 64 is illustrated as extending around a majority of the corresponding elongate electrode assembly 34, 36, 38 and 40, respectively, it will be appreciated that in some embodiments protective bumper members 58, 60, 62 and 64 may instead extend around only a portion of the respective elongate electrode assembly 34, 36, 38 and 40. For example, protective bumper member 58 may include a first portion (not illustrated) extending only around distal pad 42 and a second portion (not illustrated) extending only around proximal pad 44. Furthermore, while the term "protective" is used when describing the protective bumper members 58, 60, 62 and 64, this is not intended to be limiting. For example, the protective bumper members 58, 60, 62 and 64 may provide a number of desirable features in addition to or instead of providing "protection" to, for example, the elongate electrode assembly 34. Thus, the protective bumper members 58, 60, 62 and 64 could also be termed "bumpers", "bumper members", "edge covers", "edging", or the like.

Each of protective bumper members 58, 60, 62 and 64 may be formed of a polymer and may help to bond or secure the corresponding elongate electrode assembly 34, 36, 38 and 40 to outer surface 32. The protective bumper members 58, 60, 62 and 64 may also help to cover and protect edges of the elongate electrode assemblies 34, 36, 38 and 40 in order to help prevent electrode delamination and other possible damage to device 26 upon insertion, delivery to the therapy site, expansion of expandable member 30, contraction of expandable member 30, and withdrawal of device 26. A variety of polymeric materials may be used in forming the protective bumper members 58, 60, 62 and 64. It will be appreciated that in some embodiments, protective bumper members 58, 60, 62 and 64 may each be formed as single layers or as several distinct layers.

In some embodiments, a polymeric adhesive having a viscosity greater than about 3,000 or 4000 centipoise (cP) may be used. In some embodiments, a polymeric adhesive having a viscosity of greater than about 6,000 cP may be used. In some embodiments, a polymeric adhesive viscosity having a viscosity of greater than about 10,000 cP may be used.

In some embodiments, it will be appreciated that a desired adhesive viscosity depends, at least in part, upon the curing time of the adhesive. For example, an adhesive having a relative low viscosity may be used as long as the adhesive in question has a relatively fast cure time. Alternatively, an adhesive having a relatively long cure time may be used as long as the adhesive has a relatively high viscosity. In some embodiments, it is desirable to use a polymeric adhesive having a combination of viscosity and cure time that permits formation of a desired protective bumper profile.

A variety of different polymeric adhesives and other polymeric materials may be used. Illustrative examples include but are not limited to epoxies, acrylics, silicone, polyurethane and cyanoacrylates. In some embodiments, a light curable adhesive may be used. In some embodiments, a light curable adhesive such as those available commercially under the Loctite® name may be used. As an illustrative but non-limiting example, Loctite® 352™ may be used.

Generally, the polymeric materials selected to form protective bumper members 58, 60, 62 and 64 may be applied to device 26 using any suitable technique and may be cured using any curing process appropriate for the particular polymeric material. In some instances, the polymeric materials may be selected to provide a tough, flexible bond that is resistant to abrasion, vibration and shock.

Figure 4:
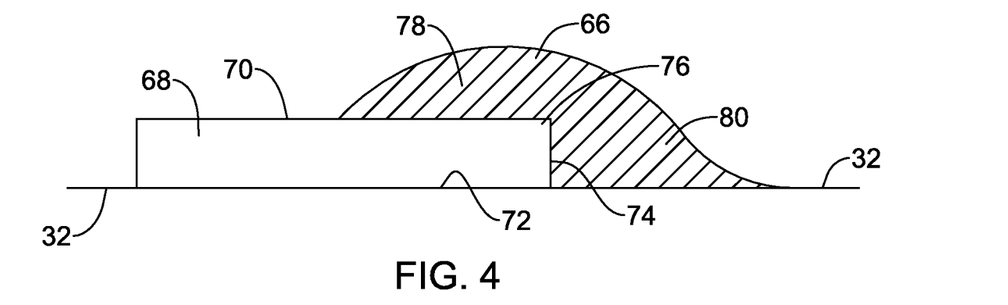
FIG. 4 is a schematic side view illustrating a portion of an electrode assembly including a protective bumper member.
Figure 5:
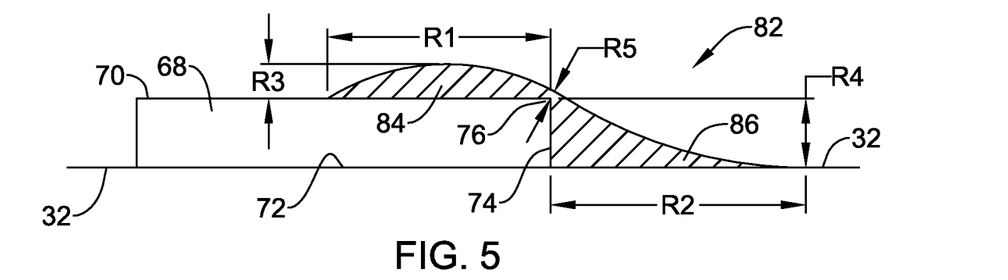
FIG. 5 is a schematic side view illustrating a portion of an electrode assembly including a protective bumper member.
Figure 6:
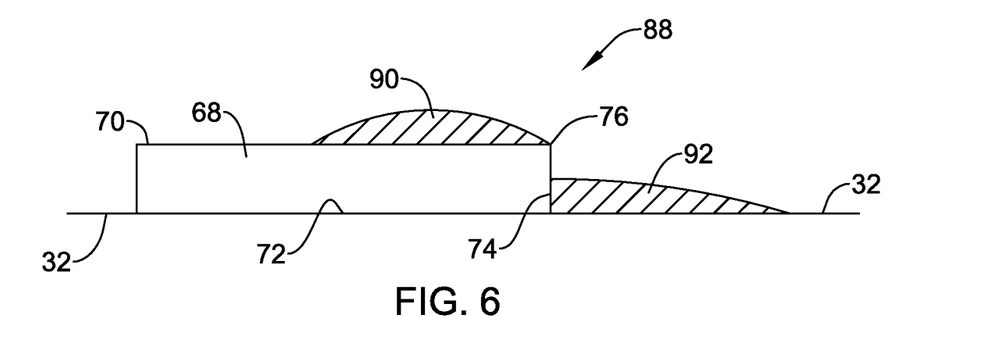
FIG. 6 is a schematic side view illustrating a portion of an electrode assembly including a protective bumper member.

FIGS. 4-6 may be considered as schematic cross-sections taken along line 4-4 of FIG. 3. Accordingly, FIGS. 4-6 may be considered as schematically showing various examples of protective bumper member 64. FIG. 4 illustrates a version of protective bumper member 64, referred to here as protective bumper member 66. Bumper member 66 can be seen as extending over a portion of an elongate electrode assembly 68. Elongate electrode assembly 68 includes an upper surface 70 and a lower surface 72 that is secured to outer surface 32. Elongate electrode assembly 68 also includes an outer edge 74 and a corner 76 disposed between upper surface 70 and outer edge 74.

In FIG. 4, protective bumper member 66 can be seen as completely covering a portion of upper surface 70, corner 76 and outer edge 74. Protective bumper member 66 may be considered as including an upper portion 78 covering a portion of upper surface 70 and a lower portion 80 extending away from elongate electrode assembly 68 along outer surface 32. While it can be seen that outer edge 74 and corner 76 of elongate electrode assembly 68 are well-protected by protective bumper member 66, in some instances protective bumper member 66 may be larger than optimal. In some instances, if the protective bumper member is too large, it can interfere with apposition of the electrode pads with a vessel wall, negatively impacting therapy efficacy or consistency thereof. In some instances, if the protective bumper member is too large, the protective bumper member can interfere with profile upon delivery. For these reasons, FIG. 4 may be considered as illustrating a less than optimal bumper member.

In FIG. 5, a protective bumper member 82 includes an upper portion 84 covering a portion of upper surface 70 and a lower portion 86 extending away from elongate electrode assembly 68 along outer surface 32. It can be seen that although outer edge 74 and corner 76 of elongate electrode assembly 68 are covered by protective bumper member 82, protective bumper member 82 has a thickness measured at corner 74 that is less than that shown, for example, in FIG. 4, but still provides a desired level of protection. FIG. 5 may be considered as illustrating an optimal bumper member.

In FIG. 6, a protective bumper member 88 includes an upper portion 90 covering a portion of upper surface 70 and a lower portion 92 extending away from elongate electrode assembly 68 along outer surface 32. It can be seen that upper portion 90 and lower portion 92 are no longer part of a contiguous bumper member, but rather are separate. Accordingly, outer edge 74 and corner 76 are not well-protected by protective bumper member 88. FIG. 6 may be considered as illustrating a poor bumper member.

Several dimensions may be useful in defining protective bumper members, and in defining the relative quality of the protective bumper member. With particular reference to FIG. 5, the upper portion of the protective bumper member (covering the upper surface of the elongate electrode assembly) may be considered as having a width R1 while the lower portion of the protective bumper member (extending along the outer surface of the expandable member) may be considered as having a width R2. Other useful dimensions include a maximum thickness R3 of the upper portion and a maximum thickness R4 of the lower portion. A thickness R5, measured at the corner of the elongate electrode assembly, may also be useful. While FIGS. 4-6 show protective bumper members in which R1 and R2 tend to remain substantially constant, it will be appreciated that in some cases R1 and/or R2 may vary.

It will be appreciated that in some cases, it may be useful to define dimensions R1, R2, R3 and R5 in terms of R4, a thickness of the elongate electrode assembly 68. For example, in some embodiments, R1 may be 2 to 20 times R4. R2 may be 2 to 20 times R4. R3 may be 1 to 20 times R4. R5 may be 1 to 14 times R4. In some instances, R4 can vary from about 0.03 millimeters (mm) to about 0.07 mm, although in some cases R4 can be outside of this range, depending on the construction of the elongate electrode assembly 68. To illustrate, the table below provides illustrative ranges for R1, R2, R3 and R5, based upon an illustrative value for R4 of 0.0015 inches (0.0381 mm).

| Dimension | Range (millimeters) |
| --- | --- |
| R1 | 0.0762-0.762 |
| R2 | 0.0762-0.762 |
| R3 | 0.0381-0.762 |
| R5 | 0.0381-0.5334 |

It will be appreciated that there may be tradeoffs in designing the dimensions of the protective bumper members. Making the protective bumper member generally larger may provide better protection to the edges of the elongate electrode assemblies, but may consume more polymeric materials and may impact flexibility and overall profile of the expandable member 30. Conversely, making the protective bumper member generally smaller may consume less polymeric material and result in a more flexible, lower profile, expandable member 30 but may not provide as much protection to the elongate electrode assembly.

In FIGS. 4 through 6, the elongate electrode assembly 68 is schematically illustrated as having a rectilinear cross-sectional profile. In some embodiments, the elongate electrode assembly 68 may have a modified edge profile that enhances adhesion, or mechanical anchorage, of the elongate electrode assembly 68 to the outer surface 32 of the expandable member 30 (see FIG. 2). In some embodiments, a modified edge profile may improve adhesion by reducing focal points of stress. A modified edge profile may, in some cases, provide for an increased adhesive surface contact area.

In some instances, the modified edge profile of the elongate electrode assembly 68 may be formed using any suitable technique. In some embodiments, the modified edge profile may be achieved by building up multiple layers having various dimensions. In some embodiments, manufacturing techniques including but not limited to sanding, scrapping, cutting, grinding, chemical etching, stamping, laser cutting, laser etching and the like may be employed. FIGS. 7 through 13 provide illustrative but non-limiting examples of modified edge profiles for the elongate electrode assembly 68. While illustrated without bumper members, it will be appreciated that in some cases the illustrated modified edge profiles may be combined with a bumper member if desired.

Figure 7:
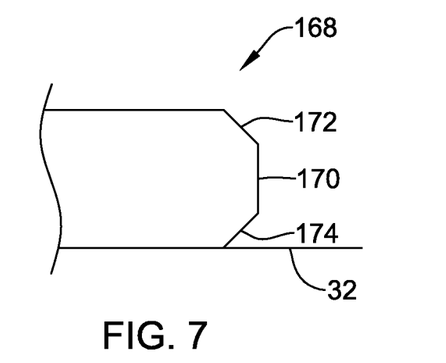
FIG. 7 is a schematic side view of a portion of an elongate electrode assembly.

FIG. 7 is a side view of a portion of an elongate electrode assembly 168 disposed on the outer surface 32 of the expandable member 30. The elongate electrode assembly 168 has a multifaceted outer edge including a first facet 170 that is substantially perpendicular to the outer surface 32 (as illustrated), a second facet 172 that angles upward from the first facet 170 and a third facet 174 that angles downward from the first facet 170. It can be seen that the third facet 174 forms, in combination with the outer surface 32 of the expandable member 30, a recessed portion that can help to secure a bumper member (not illustrated) in position, if included.

Figure 8:
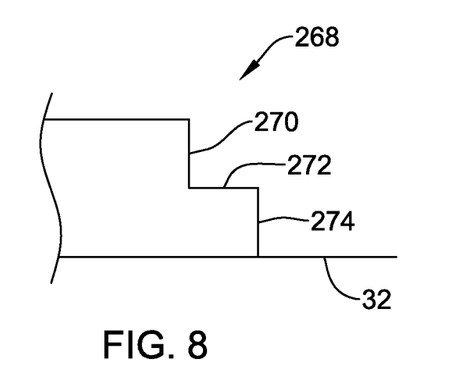
FIG. 8 is a schematic side view of a portion of an elongate electrode assembly.

FIG. 8 is a side view of a portion of an elongate electrode assembly 268 disposed on the outer surface 32 of the expandable member 30. The elongate electrode assembly 268 has a multifaceted outer edge including a first vertical (in the illustrated orientation) facet 270, a second vertical facet 274 and an intervening horizontal facet 272. The horizontal facet 272 may be considered as being orthogonal to the first vertical facet 270 and/or the second vertical facet 274. This step-wise profile may reduce stress between the expandable member 30 and the elongate electrode assembly 268.

Figure 9:
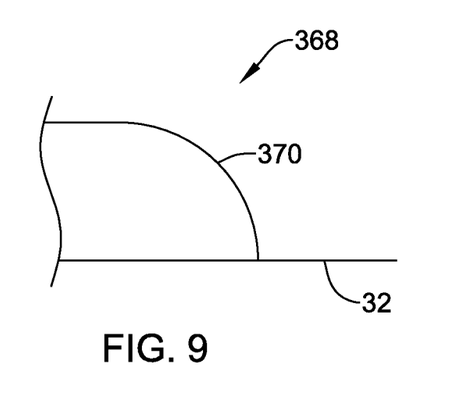
FIG. 9 is a schematic side view of a portion of an elongate electrode assembly.

FIG. 9 is a side view of a portion of an elongate electrode assembly 368 disposed on the outer surface 32 of the expandable member 30. The elongate electrode assembly 368 has a curved outer edge 370 that eliminates what would otherwise be a sharp outer edge.

Figure 10:
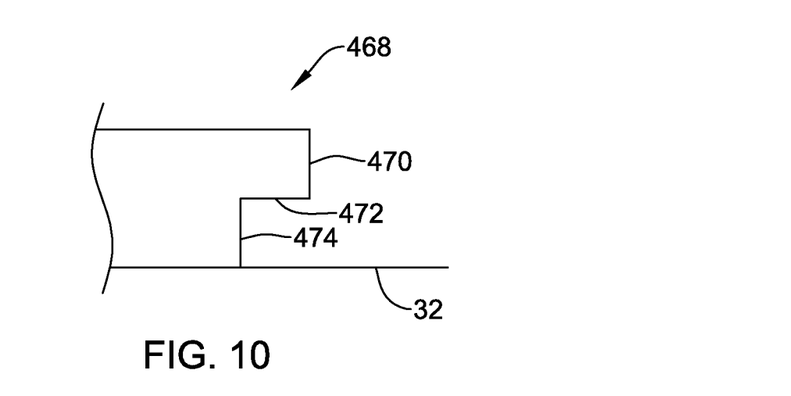
FIG. 10 is a schematic side view of a portion of an elongate electrode assembly.

FIG. 10 is a side view of a portion of an elongate electrode assembly 468 disposed on the outer surface 32 of the expandable member 30. The elongate electrode assembly 468 has a multifaceted outer edge including a first vertical facet 470, a second vertical facet 474 and an intervening horizontal facet 472. The horizontal facet 472 may be considered as being orthogonal to the first vertical facet 470 and/or the second vertical facet 474. In this embodiment, the second vertical facet 474 is stepped back from the first vertical facet 470 to form a recess that can, for example, help to hold, or secure, a portion of a bumper member (if included).

Figure 11:
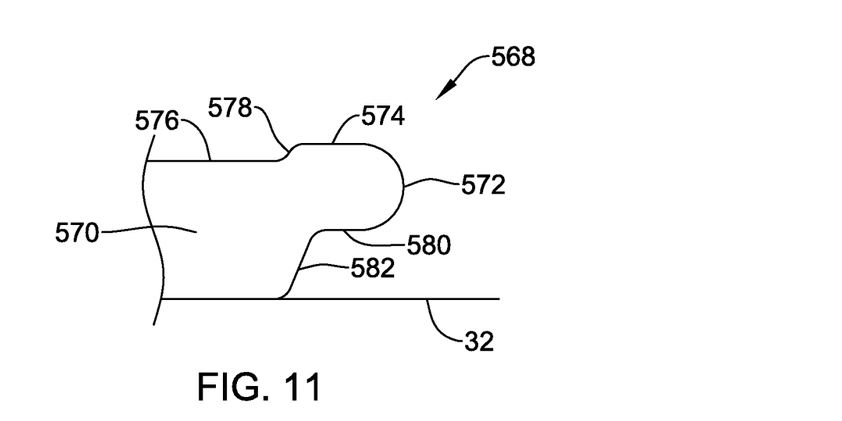
FIG. 11 is a schematic side view of a portion of an elongate electrode assembly.

FIG. 11 is a side view of a portion of an elongate electrode assembly 568 disposed on the outer surface 32 of the expandable member 30. The elongate electrode assembly 568 includes a substantially rectilinear portion 570 and a bulbous portion 572. In some embodiments, the bulbous portion 572 includes an upper surface 574 that is relatively higher above the outer surface 32 in comparison to an upper surface 576 of the substantially rectilinear portion 570, with an angled portion 578 transitioning between the upper surface 574 and the upper surface 576. The bulbous portion 572 also includes a lower surface 580 that stands above the upper surface 32 and transitions to the upper surface 32 via an angled portion 582. The elongate electrode assembly 568 may reduce stress and provide for improved bumper member adhesion.

Figure 12:
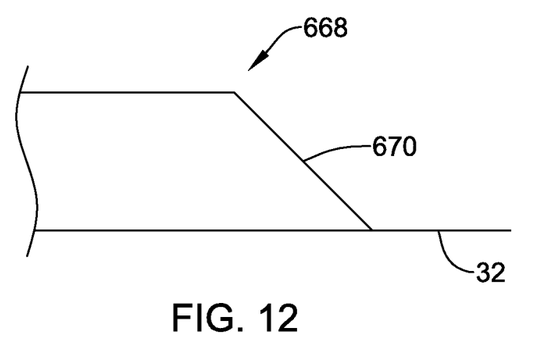
FIG. 12 is a schematic side view of a portion of an elongate electrode assembly.

FIG. 12 is a side view of a portion of an elongate electrode assembly 668 disposed on the outer surface 32 of the expandable member 30. The elongate electrode assembly 668 includes an angled facet 670 that extends downward to the outer surface 32. In some embodiments, the angled facet 670 reduces stress between the elongate electrode assembly 668 and the outer surface 32 of the expandable member 30.

Figure 13:
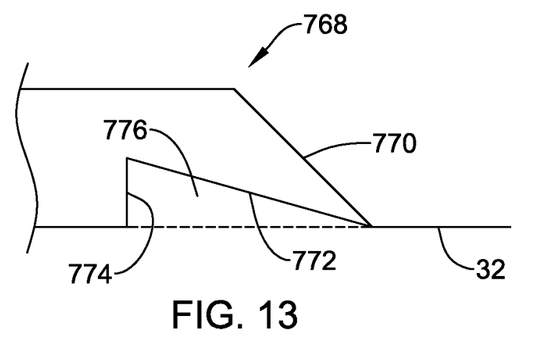
FIG. 13 is a schematic side view of a portion of an elongate electrode assembly.

FIG. 13 is a side view of a portion of an elongate electrode assembly 768 disposed on the outer surface 32 of the expandable member 30. The elongate electrode assembly 768 includes an upper angled facet 770 that extends downward to the outer surface 32. In some embodiments, as illustrated, the elongate electrode assembly 768 includes a second angled facet 772 that, in combination with an at least substantially vertical facet 774, forms an interior void 776 that can hold adhesive, thereby providing improved mechanical anchorage of the adhesive to the elongate electrode assembly 768.

FIGS. 7-13 provided illustrative but non-limiting examples of modified edge profiles in which the modification impacts an outer edge and upper edge or corner of the elongate electrode assembly. In some embodiments, the elongate electrode assembly can be modified to improve stress/strain performance by cutting or otherwise forming voids that extend into a front face of the elongate electrode assembly. FIGS. 14-19 provide illustrative but non-limiting examples of elongate electrode assemblies into which voids have been cut or otherwise formed into a front face thereof. It will be appreciated that the examples illustrated in FIGS. 14-19 may include one or more of the modified edge profiles illustrated in FIGS. 7-13.

Figure 14:
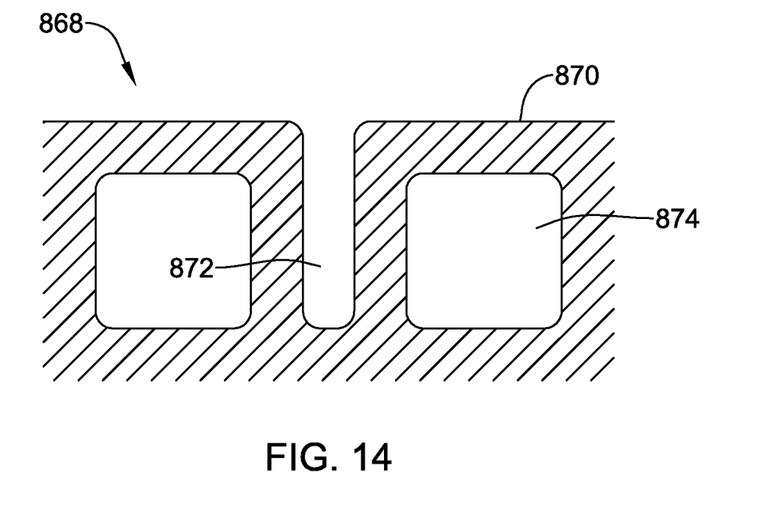
FIG. 14 is a schematic top view of a portion of an elongate electrode assembly.

FIG. 14 is a schematic top view of a portion of an elongate electrode assembly 868 having an outer edge 870. As illustrated, a rectilinear void 872 is cut into the outer edge 870. One or more voids 874 are formed within the elongate electrode assembly 868 but do not extend to the outer edge 870. The void 874 may have any desired width or length and may be proportional to the dimensions of the elongate electrode assembly 868.

Figure 15:
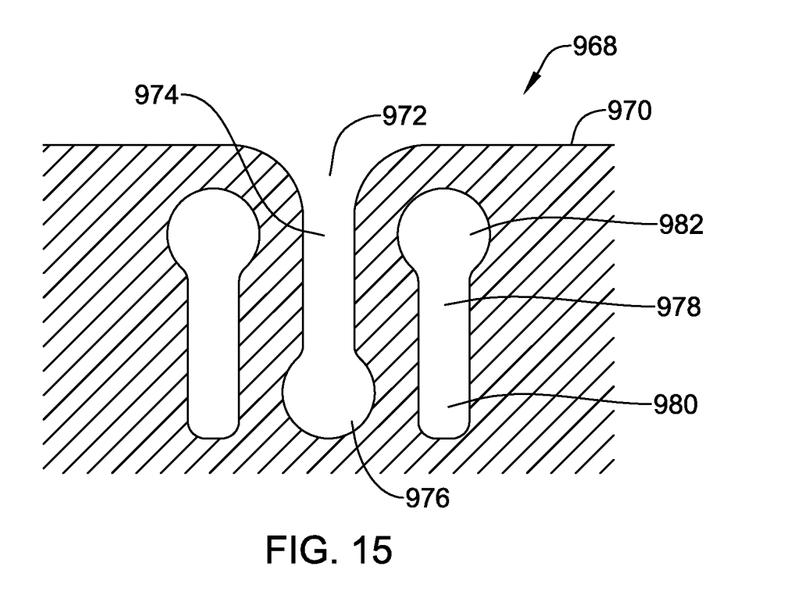
FIG. 15 is a schematic top view of a portion of an elongate electrode assembly.

FIG. 15 is a schematic top view of a portion of an elongate electrode assembly 968 having an outer edge 970. As illustrated, a void 972 is cut into the outer edge 970. The void 972 includes a rectilinear portion 974 and a circular portion 976. One or more voids 978 are formed within the elongate electrode assembly 968 but do not extend to the outer edge 970. In some embodiments, the void 978 may include a rectilinear portion 980 and a circular portion 982.

Figure 16:
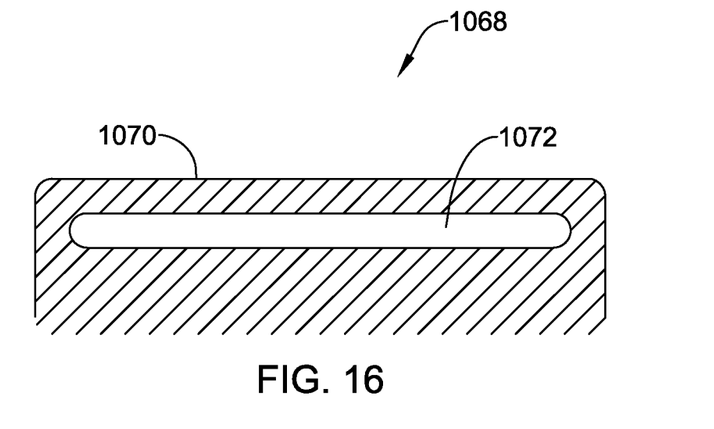
FIG. 16 is a schematic top view of a portion of an elongate electrode assembly.

FIG. 16 is a schematic top view of a portion of an elongate electrode assembly 1068 having an outer edge 1070. A void 1072 may be formed within the elongate electrode assembly 1068 but does not extend to the outer edge 1070. The void 1072 may be positioned at any desired distance from the outer edge 1070.

Figure 17:
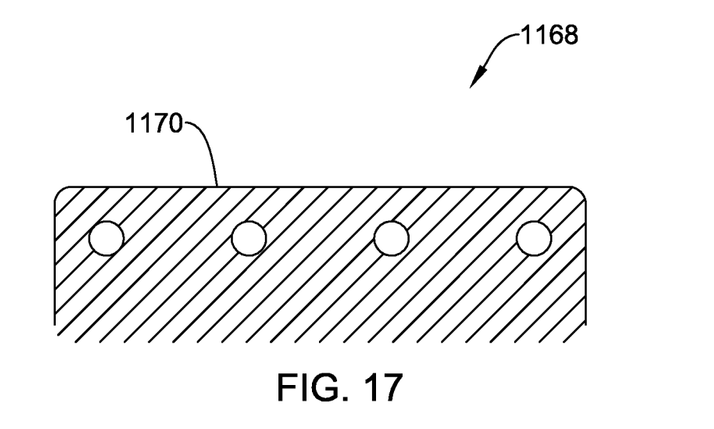
FIG. 17 is a schematic top view of a portion of an elongate electrode assembly.

FIG. 17 is a schematic top view of a portion of an elongate electrode assembly 1168 having an outer edge 1170. A series of circular voids 1172 may be formed within the elongate electrode assembly 1168 but do not extend to the outer edge 1170. The circular voids 1172 may be positioned at a relative spacing between adjacent circular voids 1172. The circular voids 1172 may be positioned at any desired distance from the outer edge 1170.

Figure 18:
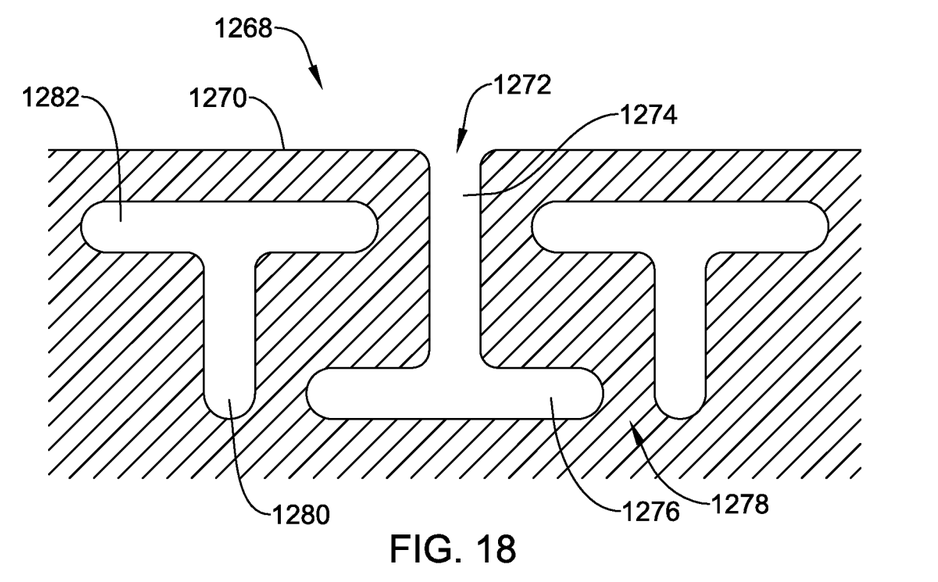
FIG. 18 is a schematic top view of a portion of an elongate electrode assembly.

FIG. 18 is a schematic top view of a portion of an elongate electrode assembly 1268 having an outer edge 1270. One or more voids 1272 are cut into the outer edge 1270. In some embodiments, the void(s) 1272 are T-shaped, having a first rectilinear portion 1274 extending from the outer edge 1270 and a second rectilinear portion 1276 that is orthogonal to the first rectilinear portion 1274. One or more T-shaped voids 1278 may be formed within the elongate electrode assembly 1268 but do not extend to the outer edge 1270. The T-shaped void(s) 1278 has a first rectilinear portion 1280 and a second rectilinear portion 1282 that is orthogonal to the first rectilinear portion 1280.

Figure 19:
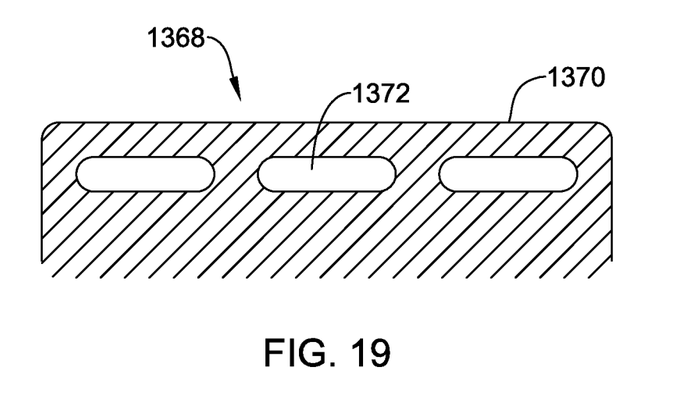
FIG. 19 is a schematic top view of a portion of an elongate electrode assembly.

FIG. 19 is a schematic top view of a portion of an elongate electrode assembly 1368 having an outer edge 1370. One or more voids 1372 may be formed within the elongate electrode assembly 1368 but do not extend to the outer edge 1370. The voids 1372 may be positioned at any desired distance from the outer edge 1370.

Catheter shaft 28 and expandable member 30 may be manufactured from various materials, including any suitable biocompatible and compliant materials, such as, but not limited to, polymers, metals, alloys, either in combination or alone. The material(s) employed may be sufficiently stiff to enable use in various lumen diameters, and be sufficiently flexible to maneuver through tortuous and/or stenotic lumens, avoiding any undesirable tissue injuries. To this end, the materials employed may include shape memory materials, such as, but not limited to, Nitinol. Other suitable materials may include polyether block amide, polyurethane, etc. In some embodiments, the material employed may have an insulating property.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Although the embodiments described above have been set out in connection with a renal nerve ablation device, those of skill in the art will understand that the principles set out there can be applied to any device where it is deemed advantageous to provide flexibility to the renal nerve ablation device. Conversely, constructional details, including manufacturing techniques and materials, are well within the understanding of those of skill in the art and have not been set out in any detail here. These and other modifications and variations are well within the scope of the present disclosure and can be envisioned and implemented by those of skill in the art.

Other embodiments of the present disclosure will be apparent to those skilled in the art from consideration of the specification and practice of the embodiments disclosed herein. It is intended that the specification and examples be considered as exemplary only, and departure in form and detail may be made without departing from the scope and spirit of the present disclosure as described in the following claims.

What is claimed is:

1. A medical device configured for nerve ablation, comprising:
    a catheter shaft;
    an expandable balloon disposed on the catheter shaft, the balloon being capable of shifting between an unexpanded configuration and an expanded configuration;
    an elongate electrode assembly constructed as a flexible circuit, the elongate electrode assembly disposed on an outer surface of the balloon and having an upper surface, an outer edge and a thickness R4 at the outer edge; and
    a protective bumper member comprising a polymeric material positioned in its entirety over the upper surface of the elongate electrode assembly and over the outer surface of the expandable balloon and covering at least a portion of the outer edge of the elongate electrode assembly, the protective bumper member extending laterally from the outer edge and onto the upper surface of the elongate electrode assembly by a first distance R1 and extending laterally from the outer edge over the outer surface of the expandable balloon and away from the elongate electrode assembly by a second distance R2, wherein R1 is 2 to 20 times R4 and R2 is 2 to 20 times R4, and wherein the protective bumper member is formed from a light curable adhesive.

2. The medical device of claim 1, wherein the protective bumper member comprises a polymeric material.

3. The medical device of claim 1, wherein the light curable adhesive has a viscosity greater than about 6000 centiPoise.

4. The medical device of claim 1, wherein the light curable adhesive has a viscosity greater than about 10,000 centiPoise.

5. The medical device of claim 1, wherein the protective bumper member covers all of the outer edge of the elongate electrode assembly.

6. The medical device of claim 1, wherein at least a portion of a bottom side of the elongate electrode assembly is attached to the outer surface of the balloon.

7. The medical device of claim 1, wherein the balloon is a non-compliant balloon and the elongate electrode assembly folds and unfolds with the balloon.

8. The medical device of claim 1, wherein the balloon is a compliant balloon and the elongate electrode assembly folds and unfolds with the balloon.

9. The medical device of claim 1, wherein the balloon comprises polyethyleneterephthalate (PET).

10. The medical device of claim 1, comprising one or more voids formed in the outer edge of the electrode assembly.

11. The medical device of claim 10, further comprising one or more additional voids formed in the electrode assembly that do not extend to the outer edge of the electrode assembly.

12. A medical device configured for nerve ablation, comprising:
   a catheter shaft;
   an expandable member coupled to the catheter shaft, the expandable member being capable of shifting between an unexpanded configuration and an expanded configuration; and
   an elongate electrode assembly constructed as a flexible circuit having a plurality of layers, the elongate electrode assembly having an upper surface and an outer edge, the elongate electrode assembly disposed on an outer surface of the expandable member and having a thickness R4 at the outer edge; and
   a protective bumper member comprising a polymeric material positioned in its entirety over the upper surface of the elongate electrode assembly and over the outer surface of the expandable member and extending about the outer edge of the elongate electrode assembly, the protective bumper member extending laterally from the outer edge and onto the upper surface of the elongate electrode assembly by a first distance R1 and extending laterally from the outer edge over the outer surface of the expandable member and away from the elongate electrode assembly by a second distance R2, wherein R1 is 2 to 20 times R4 and R2 is 2 to 20 times R4, and wherein the protective bumper member is formed from a light curable adhesive.

13. The medical device of claim 12, wherein the protective bumper member covers the outer edge and a portion of an outer periphery of the elongate electrode assembly.

14. The medical device of claim 12, wherein the protective bumper member comprises a polymeric material.

15. The medical device of claim 12, wherein the light curable adhesive has a viscosity greater than about 6000 centiPoise.

16. The medical device of claim 12, wherein the light curable adhesive has a viscosity greater than about 10,000 centiPoise.

17. The medical device of claim 12, wherein the balloon is a non-compliant balloon and the elongate electrode assembly folds and unfolds with the balloon.

18. A medical device configured for nerve ablation within a body passageway, comprising:
   a catheter shaft;
   an elongate balloon coupled to the catheter shaft, the balloon being capable of shifting between an unexpanded configuration and an expanded configuration;
   a plurality of electrode assemblies each constructed as a flexible circuit having a plurality of layers and having an upper surface, the plurality of electrode assemblies being bonded to an outer surface of the balloon, each of the plurality of electrode assemblies including an outer edge and having a thickness R4 at the outer edge; and
   a plurality of protective polymeric bumper members, each of the plurality of protective polymeric bumper members comprising a polymeric material and positioned in its entirety over the upper surface of a corresponding one of the plurality of electrode assemblies and over the outer surface of the expandable balloon and surrounding the outer edge of the corresponding one of the plurality of electrode assemblies, and each of the plurality of protective polymeric bumper members extending laterally from the outer edge and onto the upper surface of the corresponding one of the plurality of electrode assemblies by a first distance R1 and extending laterally from the outer edge over the outer surface of the expandable balloon and away from the corresponding one of the plurality of electrode assemblies by a second distance R2, wherein R1 is 2 to 20 times R4 and R2 is 2 to 20 times R4, and wherein the protective bumper member is formed from a light curable adhesive.

19. The medical device of claim 18, wherein the light curable adhesive has a viscosity greater than about 6000 centiPoise.

20. The medical device of claim 18, wherein the balloon is a non-compliant balloon.

* * * * *